United States Patent [19]

London et al.

[11] Patent Number: 4,784,842

[45] Date of Patent: Nov. 15, 1988

[54] THERAPEUTIC COMPOSITION FOR TREATMENT OF CUTS, BURNS AND ABRASIONS

[76] Inventors: Jean London; James O. Gibson, both of 351 Main St., Apt. 316, P.O. Box 998, El Segundo, Calif. 90245

[21] Appl. No.: 100,837

[22] Filed: Sep. 25, 1987

[51] Int. Cl.$^4$ .................. A61L 9/04; A01N 65/00
[52] U.S. Cl. .................. 424/45; 424/195.1; 424/238; 424/284; 424/317
[58] Field of Search .............. 424/45, 195, 196, 238, 424/284, 317, DIG. 13

[56] References Cited

U.S. PATENT DOCUMENTS 3,943,248   3/1976   Shulman ..................... 424/196.1

FOREIGN PATENT DOCUMENTS 7310429   2/1974   Netherlands ..................... 424/45

OTHER PUBLICATIONS

Pharmaceutical Aspects of Aerosols, Marsden, Pharmaeutical Journal, Conference Symposium Session, 10-2-4-64.

Primary Examiner—John E. Kittle
Assistant Examiner—P. J. Ryan
Attorney, Agent, or Firm—Max Geldin

[57] ABSTRACT

Compositions of matter and method of use of compositions consisting essentially of a mixture, in effective amounts, of (a) a terpene or mixtures thereof, and (b) vitamin E. These compositions are used for treatment of cuts, burns and abrasions of the skin in mammals, particularly humans, to facilitate healing and reduce swelling, bleeding and pain, by applying the mixture to the affected external area of the skin, as by swabbing with an applicator. Alternatively, the treatment mixture can be pressurized by means of a carrier, such as ethylene chloride, for application by spraying.

15 Claims, No Drawings

THERAPEUTIC COMPOSITION FOR TREATMENT OF CUTS, BURNS AND ABRASIONS

BACKGROUND OF THE INVENTION

This invention relates to the treatment of cuts, burns and abrasions in mammals, particularly humans, and is particularly concerned with the provision of an effective therapeutic agent and procedure employing same for the therapeutic treatment of cuts, burns and abrasions of the skin, to facilitate healing, and reduce swelling, bleeding and pain.

The initial treatment for burns is to cool the afflicted skin area and minimize swelling. The initial treatment for cuts is to stop bleeding and minimize swelling. The length of time required to completely heal cuts, burns and abrasions can be dramatically reduced if the area of the skin tissue adjacent to the wound is prevented from swelling by some suitable means. The time required for complete healing of burns can be several weeks where swelling occurs and only several days, on the other hand, where swelling was prevented. The time required for complete surface healing of deep cuts and abrasions, e.g., greater tan ⅛ inch deep, can be several months where swelling occurs and, on the other hand, only one to two weeks where swelling is prevented.

The degree and duration of pain associated with cuts, burns and abrasions is directly related to swelling. Where swelling has been prevented, the pain is substantially reduced.

The next step after swelling has been prevented is to introduce materials onto or into the injured tissue which promote healing. Vitamin E is known to promote healing of burns, and to a lesser extent, to promote healing of cuts and abrasions.

An object of the present invention is to provide an effective simple composition and method for healing cuts, burns and abrasions.

Another object is the provision of a composition and method for treating cuts, burns and abrasions of the skin in mammals, particularly humans, to promote rapid healing, while substantially reducing swelling, the level of pain and bleeding.

SUMMARY OF THE INVENTION

It has been found that the above objects and advantages are achieved according to the invention and an effective healing agent for cuts, burns and abrasions provided, in the form of a mixture or solution of a terpene and vitamin E. The terpene is generally in the form of a mixture of terpenes as in turpentine. The range of proportions of these components can vary widely, as pointed out in greater detail hereinafter, a specific effective composition being, for example, a 50—50 mixture of turpentine and vitamin E, by volume.

It has been found that the immediate application of a mixture of terpenes and vitamin E to a burn stops swelling and dramatically reduces the level of pain, the immediate application of such mixture to a severe cut substantially reduces or stops bleeding and prevents swelling and dramatically reduces pain, and the immediate application of such mixture to cuts, burns and abrasions promotes healing almost from the instant of application and dramatically reduces the time period for complete healing.

The prevention of swelling and bleeding is paramount if rapid recovery from the injury is to be achieved. Accordingly, the shorter the time interval between the instant of injury and the application of the terpene-vitamin E mixture (hereinafter "Terp-E"), the quicker swelling can be prevented, bleeding can be stopped, pain reduced, and the composition made available to promote surface and in-depth healing.

DETAILED DESCRIPTION OF THE INVENTION AND PREFERRED EMBODIMENTS

The terpene component of the invention mixture can be derived from turpentine which is composed essentially of a mixture of terpenes. Terpenes are unsaturated, organic compounds having the empirical formula $C_{10}H_{16}$ occurring in most essential oils and oleoresins of plants. The terpenes may be either open-chain or cyclic with one or more benzenoid groups and are classified as monocyclic (dipentene), dicyclic (pinene) or acyclic (mircene) according to molecular structure. Turpentine is a mixture of the terpenes, wherein α-pinene is the principal constituent. The term "turpentine" is intended as including turpentine oil and spirits of turpentine. The terpenes are essentially liquids of varying viscosity.

The vitamin E component of the "Terp-E" mixture of the invention is comprised of tocopherols, including alpha, beta, gamma and delta-tocopherol. Vitamin E is a viscous oil but is also commercially available in tablet or capsule form. When used in capsule form, the vitamin E liquid is squeezed out of the capsule and the outer coating of the capsule is discarded. Vitamin E is highly soluble in terpenes or turpentine.

The proportions of terpene (or terpenes) and vitamin E in the treatment composition of the invention can vary. Thus, there can be employed from about 10 to about 90% terpene and about 90 to about 10% vitamin E, by volume, preferably from about 65 to about 90% terpene and about 35 to about 10% vitamin E, by volume. Compositions found particularly suitable are Composition A, containing 70% terpenes, e.g., as turpentine, and 30% vitamin E, by volume, and Composition B, containing 50—50 proportions of such terpenes and vitamin E, by volume.

For treatment of cuts, burns and abrasions of the skin with the "Terp-E" composition of the invention, such composition can be applied to the afflicted area of the skin by any suitable means, such as by swabbing, for example with a Q-tip, or any other suitable applicator. Alternatively, the healing composition of the invention can be employed by direct immersion, e.g., of a finger which contains a burn, cut or abrasion, into the "Terp-E" mixture. Where found most convenient, the "Terp-E" composition can be applied to the afflicted area of the skin from a container or spray can pressurized with a suitable carrier or propellant, such as ethylene chloride, which also functions to cool the skin area adjacent the wound and aids further to prevent swelling and reduce pain. The pressurized material can comprise varying proportions of the carrier, e.g., ethylene chloride, and the "Terp-E" mixture of the invention, a suitable pressurized spray composition being comprised of about 50% by volume of the container of the terpene-E mixture, the remaining 50% volume being pressurized gas, e.g., ethylene chloride.

When applied to injured skin tissue, the terpenes tend to penetrate into the skin or skin tissue, carrying the vitamin E component, and hence, the vitamin E will also penetrate the skin or tissue and be available to promote surface and also in-depth healing. The terpenes function to stop swelling and bleeding and to reduce pain.

The terpene-vitamin E treating composition can be applied to the affected external area of the skin several times at periodic intervals to facilitate rapid healing.

The following are examples of practice of the invention:

EXAMPLE 1

Patient A was melting thin films of polyethylene and accidentally touched the liquid polyethylene with the ring finger of the right hand. The hot polyethylene stuck to the finger pad at about the center of the fingerprint. The patient applied Composition A to the affected skin area of the finger with a Q-tip within about one minute of the burn. It is believed that normally this burn with hot plastic would have produced water blisters within one or two hours.

The patient continued to apply the terpenes-vitamin E solution, Composition A, about every two to four hours for a total of three applications. The initial terpene application immediately relieved the pain, and subsequent application provided a soothing feeling to the finger. Within 24 hours, all redness had disappeared and there was substantially no evidence of a burn.

EXAMPLE 2

Patient B was washing a wine carafe in a kitchen sink and due to the soapy water, dropped the carafe. The carafe broke, and a chard of broken glass sliced the finger pad of the small finger of the left hand. The cut was very deep, almost to the bone, and progressed from the last crease of the finger toward the end of the finger. The cut was ⅝ of an inch long. The patient immediately (less than one minute) immersed the cut in Composition A.

The wound was bleeding profusely before immersion. The terpenes-vitamin E solution arrested the bleeding almost immediately because subsequent examination of the container holding the "Terp-E" indicated less than ½ cubic centimeter of blood in the container. Patient B wrapped the finger in a white cotton cloth and applied pressure to the finger pad. The patient was transported to the emergency ward of a hospital.

The resident doctor sewed the finger "flap" on with about six stitches. The doctor noted a strange odor but was not aware of the prior treatment of the finger with "Terp-E".

The patient did not have much pain the first night and thereafter continued to apply Composition A when the dressings were changed, about every two days. In about twelve days, the stitches were removed. Surface healing was complete about ten days later, and pressure could be applied to the finger pad, permitting full use of the finger. The finger healed without scarring, and the area of the flap was barely discernable.

EXAMPLE 3

Patient C reached into a microwave oven to remove a ceramic cup full of boiling water. This particular cup was poorly glazed and absorbed water into its pores and accordingly was very hot at the handle. The patient severely burned the second and third fingers of the right hand before realizing that the handle was hot and he could set the cup down.

The patient applied Composition A via Q-tips, to the second and third fingers because of the intense pain to these fingers. The pain was relieved upon application of the terpenes-vitamin E composition. The following day, the patient noted that the fourth finger (the side of the finger which pressed up against the cup handle) was blistered. This finger did not receive application of Composition A. The second and third fingers which received a more severe burn and did receive application of Composition A did not blister.

The fourth finger took the normal course of healing since it blistered. Three weeks elapsed before complete replacement of new skin and loss of scabs. The second and third fingers showed no evidence of burns after the second day.

EXAMPLE 4

Patients D and E were badly skinned over substantial portions of their bodies as a result of being thrown from a small truck in an accident. The patients were taken to a hospital and were released three days later. Patient D had deep abrasions on forearms, elbows, knees, shins, etc. Scabs were up to 2 inches wide and up to 6 inches long. Patient E had similar cuts, abrasions and scabs. Patients D and E had difficulty and pain in moving, walking and stretching due to the tightness and rigidity of the scabs.

Patient D accepted the application of treatment with Composition A to the scabs and wounds (approximately four days after the accident). The treatment composition was applied three times per day initially for two days and twice per day thereafter for three days. Patient D noticed an immediate soothing effect from the treatment and a flexibility or softness in the scabs which made it easier to move and walk without discomfort. The scabs on patient D began coming off three days after the start of the application of Composition A and nearly all scabs were gone after five days. Beneath each scab was a healthy pink new skin.

Patient E, who was not treated with Composition A, had continued discomfort from the scabs when moving or walking due to the stiffness or inflexibility of her scabs. This patient still had scabs four weeks after Patient D's scabs were gone. Patient E did use antibiotic salves applied to her scabs.

This example illustrates that even with delayed use of Composition A, such treatment still provided benefical effects and significantly reduced healing times over the other patient who did not use Composition A at all.

EXAMPLE 5

Patient F suffered cuts and burns on both the left and right forearms.

Composition B, 50% spirits of turpentine and 50% vitamin E liquid, by volume, was applied to a cut and burn on the right forearm immediately, but it was not applied to a cut and burn on the left forearm. The vitamin E liquid was obtained from commercially available vitamin E capsules containing dl-alpha tocopheryl acetate, by squeezing the liquid from the capsules and discarding the outer covering of the capsules.

After about 3 hours, the cut on the right arm had already commenced healing over a substantial portion thereof, and the burn on the right arm did not show any indication of swelling and appeared to be healing back onto the skin layer beneath.

The cut on the left forearm, which was not treated with Composition B, was very red and had not pulled together. The burn on this arm was noticeably puffed with swelling above the surrounding skin area.

The above examples demonstrate that application of the terpene-vitamin E composition of the invention to cuts, burns and abrasions provides extremely rapid healing of the wound, with substantial reduction of swelling, pain and bleeding, and with no adverse side effects.

Since various changes and modifications of the invention can be made without departing from the spirit thereof, the invention is not to be taken as limited except by the scope of the appended claims.

What is claimed is:

1. A therapeutic composition for the treatment of cuts, burns and abrasions which consists essentially of a mixture containing (a) about 10 to about 90% of a substance selected from the group consisting of a terpene and mixtures thereof, and (b) about 90 to about 10% of vitamin E, by volume.

2. The composition of claim 1, said mixture containing about 65 to about 90% of said substance and about 35 to about 10% vitamin E, by volume.

3. The composition of claim 1, said substance being turpentine.

4. The composition of claim 1, said substance being turpentine and said mixture containing about 70% turpentine and about 30% vitamin E, by volume.

5. The composition of claim 1, said substance being turpentine, and said mixture containing about 50% turpentine and about 50% vitamin E, by volume.

6. The composition of claim 1, said mixture being present in a pressurized carrier for spraying.

7. The composition of claim 6, said carrier being ethylene chloride.

8. A method of treating cuts, burns and abrasion of the skin in mammals to facilitate healing and reduce swelling, bleeding and pain, which comprises contacting the affected external area of the skin with a composition which consists essentially of a mixture containing (a) about 10 to about 90% of a substance selected from the group consisting of a terpene and mixtures thereof, and (b) about 90 to about 10% of vitamin E, by volume.

9. The method of claim 8, wherein the affected external area of the skin is contacted at periodic intervals with said mixture.

10. The method of claim 8, said mixture containing about 65 to about 90% of said substance and about 35 to about 10% vitamin E, by volume.

11. The method of claim 8, wherein said substance is a mixture of terpenes.

12. The method of claim 8, said contacting being carried out by spraying said mixture in a pressurized carrier onto the affected external skin area.

13. The method of claim 12, wherein said carrier is ethylene chloride.

14. The composition of claim 1, wherein said substance is α-pinene.

15. The method of claim 8, wherein said substance is α-pinene.

* * * * *